US006548052B2

(12) United States Patent
Rosenberg Nevo

(10) Patent No.: US 6,548,052 B2
(45) Date of Patent: *Apr. 15, 2003

(54) ANTIBACTERIAL DEODORIZING COMPOSITIONS

(75) Inventor: Melvyn Rosenberg Nevo, Ramat-Gan (IL)

(73) Assignee: Innoscent Ltd., Ramat-Gan (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/519,257

(22) Filed: Mar. 6, 2000

(65) Prior Publication Data

US 2002/0136702 A1 Sep. 26, 2002

Related U.S. Application Data

(63) Continuation of application No. PCT/IL98/00415, filed on Aug. 27, 1998.

(30) Foreign Application Priority Data

Sep. 4, 1997 (IL) .................................. 121709

(51) Int. Cl.$^7$ .............................. A61L 9/01; A61K 7/06; A61K 35/78
(52) U.S. Cl. .................... 424/76.1; 424/74; 424/725
(58) Field of Search .................... 424/74, 76.1, 725

(56) References Cited

U.S. PATENT DOCUMENTS 4,569,839 A * 2/1986 Grollier et al. ............... 424/74
5,318,778 A 6/1994 Schmucker et al.

FOREIGN PATENT DOCUMENTS

| DE | 4341647 | 6/1995 |
| DE | 4402203 | 7/1995 |
| DE | 4410162 | 9/1995 |
| DE | 19607220 | 7/1997 |

OTHER PUBLICATIONS

Bhatnagar et al. "Biological Activity of Indian Medicinal Plants", Ind. J. Med. Res. 49:799–813 (1961).*
Abstract of Japan JP 61–143315 (1986).
Al–Yahya M. A. *Phytochemical Studies of Lants Used in Traditional Medicine of Saudi Arabia*, fizoterapia vol. 57, No. 3, 1986, pp. 179–182.
Z. F. Mahmoud et al. *Constituents of Henna Leaves Growing in Egypt*, Fitoterapia, 51:153–155 (1980).
O. Hoffmann, W. Ostenhof and O. Krapupp, *Bacteriostatic quinones and other antibiotics*, Montsh. Chem. 77:86–96 (1947).
K.K. Anand, D. Chand, B.J. Rah Ghatak, and R.K. Arya, *Histological Evidence of Protection by Indigofera Tinctoria Linn. Against Carbontetrachloride Induced Hepatotoxicity—An Experimental Study*, Indian Journal of Experimental Biology, 19: 298–300 (1981).
S.S. Bhatnagar et al. *Biological Activity of Indian Medicinal Plants*, Ind. J. Med. Res. 49: 799–813, (1961).
F. Malekzadeh, *Antimicrobial Activity of Lawsonia Inermis L.*, Applied Microbiology. 16:663–664 (1968).
N. Didry, L. Dubreuil and M. Pinkas, *Activity of Anthraquinonic Compounds on Oral Bacteria*, Pharmazie, 49:681–683 (1994).
Handbook of Medicinal Herbs, p. 274.
Karawya et al. (M.S. Karawya, A.S.M. Wahha and A.Y. Zaki) *A study of Lawsone content in Henna*, Lloydia, 32:76 (1969).
K.K. Anand, D. Chand, and B.J. Rah Ghatak, *Protective effect of Alcoholic Extract of Indigofera tinctoria Linn. in experimental Liver injury*, Indian Journal of Experimental Biology, 19:685–687 (1979).
English Translation of Chisik B.: Treasure of Plants vol. 1, p. 333, and.
R. Han, *Highlight on the Studies of anticancer drugs derived from Plants in China*, Stem Cells 12: 53–63 (1994).

* cited by examiner

Primary Examiner—Thurman K. Page
Assistant Examiner—Blessing Fubara
(74) Attorney, Agent, or Firm—Merchant & Gould PC

(57) ABSTRACT

A deodorizing composition comprising as an antimicrobial agent an effective amount of an extract of *Indigofera tinctoria*, or of an antimicrobially active fraction thereof.

10 Claims, No Drawings

ANTIBACTERIAL DEODORIZING COMPOSITIONS

This is a continuation of copending International application No. PCT/IL98/00415 filed Aug. 27, 1998.

FIELD OF THE INVENTION

The present invention relates to deodorizing compositions. More particularly, the invention relates to antimicrobial deodorizing compositions for this purpose.

BACKGROUND OF THE INVENTION

Body odor is formed when fresh perspiration, which is odorless per se, is decomposed by microorganisms. This process takes place principally, though not solely, in the axilla, and a number of microorganisms are involved, each having different activity and leading to body odor of different strength and unpleasantness. The most prominent odor-producing microorganisms include aerobic diphtheroids, primarily Corynebacterium species and coagulase negative cocci such as Micrococcaceae.

Various microorganisms are found in different proportions in different individuals, and this is a reason for the fact that different individuals exhibit different body odors.

The commercial cosmetic deodorants are based on different active principles. The formation of perspiration is suppressed according to the known art by astringents, predominantly aluminum salts such as aluminum hydroxychloride. Apart from the denaturation of the skin proteins, however, the substances used for this purpose clog the pores, interfere drastically with the heat regulation of the axillary region, may cause cancer and other diseases, and should at best be used in exceptional cases. According to another accepted prior art method, the bacterial flora on the skin is reduced by antimicrobial substances. Finally, body odor can also be concealed by fragrances, which, however, is the least able to meet the aesthetic needs of the consumer, as the mixture of body odor and perfume fragrance smells rather unpleasant.

According to a recent patent on this subject (U.S. Pat. No. 5,318,778), deodorants should fulfill the following conditions:

1) The biological processes of the skin must not be impaired.
2) The deodorants should have no distinct intrinsic odor.
3) They must be harmless in the case of overdosage or other unintended use.
4) They should not concentrate on the skin after repeated use.
5) It should be possible to incorporate them easily into commercial cosmetic formulations.

Those which are known and usable are both liquid deodorants, for example aerosol sprays, roll-ons and the like and solid preparations, for example deodorant sticks, powders, powder sprays, intimate cleansers etc.

U.S. Pat. No. 5,318,778 approaches the problem by employing antibiotics, which are said to be specific microbiocides which predominantly destroy odor-forming microorganisms.

All the prior art methods suffer from severe drawbacks: they require the masking of body odor which has already formed prior to the application of the deodorant, because the destruction of axillary microorganisms does not remove already formed odor. They require the use of antimicrobial agents which must have a long-lasting activity on the skin, because the skin flora is not completely exterminated by their application, and, quite importantly, they very often leave unpleasant stains or halos on the cloths, particularly at and around the axilla. Also the safety of many antiperspirants is dubious, due to the presence of potentially harmful components, and the result is often unpleasant, because of the unnatural odor obtained.

Notwithstanding the many efforts made during many years, and the magnitude of the problem involved, the art has failed to provide deodorizing compositions which are convenient and safe to use, which are effective for a long time. The inventors have now surprisingly found, and this is an object of the invention, that the aforesaid goals can be achieved by using a well known harmless and effective natural agent: Henna.

Henna (*Lawsonia inermis*) is a small shrub growing in Arabia, North Africa, Iran and the East Indies. Dried leaves are a source of green powder used in cosmetics. Although henna paste has been used as a remedy for boils, wounds and some mycotic infections, there are few data on the activity of extracts.

S. S. Bhatnagar et al. [Biological activity of indian medicinal plants. Ind. J. Med. Res. 49: 799–813, 1961] examined antibacterial, antitubercular and antifungal action of 351 Indian plants. The extraction method was first using petrol (b.p. 40–60° C.), followed by extraction of the extracted powder with either 90% or 10% methanol. They found that henna powder was active against all three categories, although they did not list the kind of extracts which were active. One of the few scientific papers discussing extraction of henna for antibacterial activity is that of F. Malekzadeh [Antimicrobial activity of *Lawsonia inermis* L., Applied Microbiology, 16:663–664, 1968]. He studied aqueous extracts and found that while both Gram + and Gram − bacteria were inhibited, inhibitory action was greatest against *Bacillus anthracis* and least against *Staphylococcus aureus*.

One known component of henna is lawsone, a napthoquinone pigment which has antibacterial activity against oral species. [N. Didry, L. Dubreuil and M. Pinkas, Activity of anthraquinonic and naphthoquinonic compounds on oral bacteria, Pharmazie, 49:681–683, 1994].

While henna has been used since biblical times as a colorant, and has been mentioned anecdotally as an antiperspirant and antibacterial agent and as a source of gallic acid which inhibits "*Streptococcus aureus*" slightly [Handbook of Medicinal Herbs, p. 274], the direct use of henna extract has been always limited due to its high staining power, which is undesirable both to skin and clothing.

Z. F. Mahmoud et al. [Constituents of Henna Leaves Growing in Egypt, Fitoterapia, 51:153–155, 1980] isolated seven crystalline compounds from Egyptian henna leaves. They write that henna has been used for preserving mummies, and has been used for skin diseases and tinea of the legs. They extracted powdered leaves at room temperature with ethanol. The ethanolic extract was concentrated under vacuum and partitioned between chloroform and water. The aqueous layer was successively extracted with ethyl acetate, etc. They cite that the lawsone, the dyeing principle of henna has bacteriostatic properties, citing the work of Karawya et al. [M. S. Karawya, A. S. M. Wahha and A. Y. Zaki, A study of the lawsone content in henna, Lloydia, 32:76, 1969].

Karawya et al. did not actually check antibacterial activity, but rather established a simple method for estimating the quantity of lawsone. They also mention antifungal and antibacterial properties, citing the work of Hoffman et al. [O. Hoffmann, W. Ostenhof and O. Krapupp. Bacteriostatic quinones and other antibiotics. Montsh. Chem. 77:86–96, 1947].

Black Henna, according to the information given by Alban Muller International, is a mixture of henna powder, and black powder from the plant *Indigofera tinctoria*. According to Anand et al. [K. K. Anand, D. Chand and B. J. Rah Ghatak, Protective effect of alcoholic extract of *Indigofera tinctoria* Linn. in experimental liver injury, Indian Journal of Experimental Biology,19:685–687, 1979], *I. tinctoria* is an annual herbaceous shrub 4–6 feet high found throughout India. It was cultivated in India, China and other countries of the east as a source of Indigo (a colorant that dates back to biblical times, according to B. Chisik in his book in Hebrew, "Treasure of plants" (Otzar Ha'Tsmachim), Vol. 1, p. 333, Hertzlia, Hotzahat Hamechaber, Tsi"b). The extract of the plant is used in epilepsy, nervous disorders and bronchitis. The authors extracted the aerial part of the plant (powdered) with 50% alcohol. They then checked and found marked antihepatotoxic effect in animals.

In another paper (K. K. Anand, D. Chand, B. J. Rah Ghatak, and R. K. Arya, histological evidence of protection by *Indigofera tinctoria* Linn. against carbontetrachloride induced hepatotoxicity—an experimental study, Indian Journal of Experimental Biology, 19: 298–300, 1981), the authors presented histological evidence for protection of liver cells, against carbontetrachloride induced hepatotoxicity using a 50% ethanolic extract.

In another article by R. Han (Highlight on the studies of anticancer drugs derived from plants in China, Stem Cells 12:53–63, 1994), the author reports that indirubin from *Indigofera tinctoria* is useful for the treatment of chronic myelocytic leukemia.

The fact that henna extracts have never been considered for use in respect of body odor control is probably related, inter alia, to the fact that henna extract retain a high staining power and thus any composition containing such extract is inherently deleterious to clothing and is not to be considered for application to the skin in the vicinity of clothing.

It is an object of the present invention to provide body-odor controlling compositions containing henna extracts, which are efficient to control skin microorganisms which are responsible for body odor.

It is another object of the invention to provide such deodorizing composition based on henna extracts, which can be used to control body odor, without incurring the risk of staining clothing.

It is yet another object of the invention to provide deodorizing compositions which are selective toward specific skin microorganisms, and that therefore permit to control body odor without harming the natural flora of the skin.

It is still another object of the invention to provide a method for deodorizing human or animal skin, and for preventing the formation of body odor.

It is a further object of the invention to provide a process for manufacturing a deodorizing composition of the invention.

Other objects and advantages of the invention will become apparent as the description proceeds.

SUMMARY OF THE INVENTION

In one aspect, the invention is directed to a deodorizing composition comprising as an antimicrobial agent an effective amount of an extract of *Lawsonia inermis*, or of an antimicrobially active fraction thereof.

According to one preferred embodiment of the invention the deodorizing composition further comprises materials extracted from *Indigofera tinctoria*.

It is possible, to include in the deodorizing composition according to the invention additional conventional deodorant components, such as antibacterial and antiodor materials, e.g., essences, such as essential oils, triclosan, triethyl citrate.

The deodorizing composition of the invention is particularly suitable for use as a pre-shower deodorant. Thus, it is possible to apply the composition of the invention and then to remove it using regular detergents. Thus, the objects of the invention are achieved but not undesirable staining of clothing takes place.

In another aspect the invention is directed to a process for manufacturing a deodorizing composition, which process comprises extracting natural material comprising *Lawsonia inermis* with a suitable extraction solvent, and using the extract so obtained as such, or in a suitable carrier. Such suitable carriers may be chosen, but are not limited to a group of aqua, alcohol and oil based carriers such as water, ethanol and isopropylmyristate, respectively.

In a further aspect, the invention is directed to a process for manufacturing a deodorizing composition, said process comprising extraction of natural material comprising *Indigofera tinctoria* with a suitable extraction solvent, and using the extract so obtained as such, or in a suitable carrier.

According to a preferred embodiment of the invention, when the natural material employed as raw material in the process is derived from *Lawsonia inermis,* said natural material may further comprise natural material derived from *Indigofera tinctoria*. Suitable raw materials for the process of the invention are red henna and black henna.

While the invention is not limited to the use of any particular raw material, or any particular form of raw material, according to a preferred embodiment of the invention the raw material employed for the extraction process is a henna powder.

The invention, inter alia, is directed also to a method for deodorizing and/or preventing the formation of body odors, comprising applying to the axilla and/or other body part affected by body odor a deodorizing composition comprising as an antimicrobial agent an effective amount of an extract of *Lawsonia inermis*, or of an antimicrobially active fraction thereof, for a period of time sufficient to inhibit the growth of skin microorganisms responsible for body odor formation, and then washing off the deodorizing composition using conventional detergents.

Similarly, the invention is also directed to a method for deodorizing and/or preventing the formation of body odors, comprising applying to the axilla and/or other body parts affected by body odor a deodorizing composition comprising as an antimicrobial agent and effective amount of an extract of *Indigofera tinctoria*, or of an antimicrobially active fraction thereof, for a period of time sufficient to inhibit the growth of skin microorganisms responsible for body odor formation, and then washing off the deodorizing composition using conventional detergents.

In another aspect, the invention is directed to an antimicrobial composition comprising an extract of *Indigofera tinctoria* or *Indigofera tinctoria*-containing material. The invention also specifically makes provision for an antimicrobial composition effective against *Staphylococcus aureus,* said composition comprising an extract of of *Indigofera tinctoria* or *Indigofera tinctoria*-containing material. The aforementioned extract may be produced using one of several different extracting solutions, including aqueous, and alcohol in water. In the latter case, according to a preferred embodiment, the concentration of alcohol in the water is in the range of 10 to 30 %. While several different alcohols may be used, a preferred alcohol is ethanol.

In a further aspect, the invention is directed to the use of *Indigofera tinctoria* extracts as an antimicrobial agent effective against *Staphylococcus aureus*. It has been surprisingly found, as will be apparent to the skilled person, from the detailed description to follow, that extracts of *Indigofera tinctoria* and of black henna, which contain *Indigofera tinctoria*, are very effective in the inhibition of *Staphylococcus aureus* growth, while red henna, which does not contain *Indigofera tinctoria*, is only partially effective (see, e.g., Table VII).

In another aspect, the invention is directed to an antimicrobial composition comprising an extract of *Lawsonia inermis*-containing material. The invention also specifically makes provision for an antimicrobial composition effective against Corynebacterium species, said composition comprising an extract of *Lawsonia inermis*-containing material. The aforementioned extract may be produced using one of several different extracting solutions, including aqueous, and alcohol in water. In the latter case, according to a preferred embodiment, the concentration of alcohol in the water is in the range of 10 to 30%. While several different alcohols may be used, a preferred alcohol is ethanol.

The invention further provides for the use of a *Lawsonia inermis* extract as an antimicrobial agent for the inhibition of Corynebacterium species.

DETAILED DESCRIPTION OF PREFERRED EMBODIMENTS

The above and other characteristics and advantages of the invention will be more readily apparent through the following examples of preferred embodiments thereof

General Procedures

The Extraction Process: One ml of solvent was added to 0.1–0.2 gr of henna powder. The mixture was vortexed for 10 min and the samples were centrifuged for 30 min at 10000 rpm. The supernatant was collected and referred to as the extract. The extract was then filtered through a 0.22 or a 0.45 μm filter.

Following centrifugation, the extract was allowed to stand at room temperature. It was noted that despite the previous centrifugation and filtration, a fine dark precipitate slowly collected towards the bottom of the aliquots. The amount of precipitate decreased as the percentage of alcohol increased. When this was observed, it was decided to check whether this precipitation resulted in a difference in antibacterial activity. The extract was centrifuged for an additional 30 min at 10000 rpm, and the upper layer (relatively free from precipitate) and the lower layer (rich in precipitate) were separated and tested separately for antibacterial activity. Almost no difference was found between the diameter of the inhibition zones, although the lower phase (rich in precipitate) formed a more transparent inhibition zone.

Inhibition Test: The antimicrobial activity of the various extracts was examined by applying samples (5 μl) onto lawns of axillary bacteria. Following incubation of 24 hours at 37° C., inhibition was determined by measuring the diameter of the growth inhibition zone (in cm). In the tables, "+" indicates full growth inhibition(transparent zone), "−" indicates lack of inhibition, and "+/−" indicates partial inhibition (translucent zone).

Comparative Testing

For the purposes of comparative testing, 5 μl aliquots of either red or black henna extracts (20% w/v in 20% v/v ethanol) are applied to the bacterial lawns.

Red henna extract is considered active when:
1. (a) it inhibits the growth of *C. xerosis,*
   (b) the inhibition zone is transparent or translucent, and
   (c) the diameter of the inhibition zone is greater then 0.5 cm, and
2. it does not inhibit the growth of *S. epidermidis* (although in some cases, a translucent "inhibition" zone is seen).

Black henna extract is considered active when:
1. (a) it inhibits the growth of *C. xerosis,*
   (b) the inhibition zone is transparent or translucent, and
   (c) the diameter of the inhibition zone is greater then 0.5 cm, and
2. (a) it inhibits the growth of *S. epidermidis,*
   (b) the inhibition is transparent, and
   (c) the diameter is bigger then 0.5 cm.

Some purified components of henna (according to the specification sheet given by Alban Muller International) were tested, and no activity similar to that described herein was found. Solutions of lawsone, 1,4-naphthoquinone and gallic acid were tested for growth inhibition of *Staphylococcus eidermidis* and *Corynebacterium xerosis*.

The results are detailed in Table I below:

TABLE I

| component | solvent | Inhibition of S. epidermidis | Inhibition of C. xerosis |
| --- | --- | --- | --- |
| lawsone 0.2% | ethanol 20% | − | − |
| lawsone 0.02% | ethanol 20% | − | − |
| lawsone 0.01% | ethanol 20% | − | − |
| 1,4-naphthoquinone 0.2% | ethanol 20% | +, 1.4 cm | +, 0.8 cm |
| 1,4-naphthoquinone 0.02% | ethanol 20% | − | − |
| 1,4-naphthoquinone 0.01% | ethanol 20% | − | − |
| gallic acid 0.4% | ethanol 20% | +/− | − |
| gallic acid 0.2% | ethanol 20% | − | − |
| lawsone 1.0% | hot water | − | − |
| lawsone 1.0% | ethanol 50% | − | − |
| lawsone 1.0% | ethanol 100% | − | − |

Although 1,4-naphthoquinone which is supposed to be found in henna leaves inhibits the growth of the two strains, it seems that the activity which the inventors have found is not due to this component as the extract of red henna of the invention inhibits only *C. xerosis*.

EXAMPLE 1

Operating as in the General Procedures above, commercial extracts of henna were tested against *S. epidermidis* and *C. xerosis*. The results are shown in Table II. It can be seen that all extracts were active against *C. xerosis*, but only the first extract (which is a blend of *Lawsonia inermis* and *Indigofera tinctoria*) caused a full growth inhibition of *S. epidermidis*.

TABLE II

| SOURCE & COLOR OF Henna | EXTRACTION CONDITIONS, SOLVENT AND EXTRACT COLOR | INHIBITION OF S.epidermidis | INHIBITION OF C.xerosis |
| --- | --- | --- | --- |
| Alban Muhler black henna AMI watersoluble | no data, water/ propylene glycol, brown | +2.0 cm | +, 0.8 cm |

TABLE II-continued

| SOURCE & COLOR OF Henna | EXTRACTION CONDITIONS, SOLVENT AND EXTRACT COLOR | INHIBITION OF S.epidermidis | INHIBITION OF C.xerosis |
|---|---|---|---|
| H&R-Cremogen henna neutral | no data, water/dipropylene glycol, dark brown | – | +/–, 1.0 cm |
| Gattefosse-Vegetol henna | prolonged maceration of the leaves in water/propylene glycol. brown | – | +, 0.7 cm |
| Vege-Tech henna neutral | no data, water, Amber | +/–, 1.2 cm | +, 2.0 cm |

EXAMPLE 2

In order to ascertain the effect of the extracting agents ethanol and methanol employed in the extractions, the inhibition of *S. epidermidis* and *C. xerosis* by these solvents was tested. The results are shown in Table III.

The results show that some inhibition of *C. xerosis* is caused by ethanol, above 40% (v/v) in water, and by methanol above 45%, while no inhibition was found for *S. epidermidis*.

TABLE III

| ETHANOL Content | INHIBITION OF C. xerosis | INHIBITION OF S.epidermidis | METHANOL Content | INHIBITION OF C. xerosis | INHIBITION OF S.epidermidis |
|---|---|---|---|---|---|
| 5% | – | – | 5% | – | – |
| 10% | – | – | 10% | – | – |
| 15% | – | – | 15% | – | – |
| 20% | – | – | 20% | – | – |
| 25% | – | – | 25% | – | – |
| 30% | – | – | 30% | – | – |
| 35% | – | – | 35% | – | – |
| 40% | +/–, 0.2 cm | – | 40% | – | – |
| 45% | +/–, 0.2 cm | – | 45% | +/– | – |
| 50% | +/–, 0.6 cm | – | 50% | +/– | – |
| 55% | +/–, 0.6 cm | – | 55% | +/– | – |
| 60% | +/–, 0.8 cm | – | 60% | +/–, 0.8 cm | – |
| 65% | +/–, 0.8 cm | – | 65% | +/–, 0.8 cm | – |
| 70% | +/–, 0.8 cm | – | 70% | +/–, 0.8 cm | – |
| 75% | +/–, 0.8 cm | – | 75% | +/–, 0.8 cm | – |
| 80% | +/–, 0.8 cm | – | 80% | +/–, 0.8 cm | – |
| 90% | +, 1.1 cm | – | 90% | +/–, 0.8 cm | – |
| 100% | +, 1.3 cm | – | 100% | +/–, 0.8 cm | – |

EXAMPLE 3

Operating as in the General Procedures above, ethanolic extracts of black henna were tested against *S. epidermidis* and *C. xerosis*. The results are shown in Table IV.

TABLE IV

| SOURCE & COLOR OF HENNA | EXTRACTION CONDITIONS AND EXTRACT COLOR | INHIBITION OF S.epidermidis | INHIBITION OF C.xerosis |
|---|---|---|---|
| Market B1-black henna powder | water, black | +, 0.8 cm | +/– |
| | ethanol 10%, dark brown + black powder | +, 2.0 cm | +, 0.8 cm |
| | ethanol 15%, dark brown + black powder | +, 2.2 cm | +, 0.8 cm |
| | ethanol 20%, dark brown + black powder | +, 2.0 cm | +, 0.8 cm |
| | ethanol 25%, dark brown + black powder | +, 2.0 cm | +, 0.8 cm |
| | ethanol 30%, dark brown + black powder | +, 2.0 cm | +, 0.8 cm |
| | ethanol 35%, dark brown + black powder | +, 2.0 cm | +, 0.8 cm |
| | ethanol 40%, brown | +, 1.0 cm | +, 0.8 cm |
| | ethanol 45%, brown | +, 1.0 cm | +, 0.8 cm |
| | ethanol 50%, brown | +, 1.0 cm | +, 0.8 cm |
| | ethanol 55%, brown | +, 1.0 cm | +, 0.8 cm |
| | ethanol 60%, dark brown | +, 1.0 cm | +, 0.8 cm |
| | ethanol 65%, dark brown | +, 1.0 cm | +, 0.8 cm |
| | ethanol 70%, dark brown | +, 1.0 cm | +, 0.8 cm |
| | ethanol 75%, dark brown | +, 1.0 cm | +, 1.1 cm |
| | ethanol 80%, brown-black | +, 1.0 cm | +, 1.1 cm |
| | ethanol 85%, brown-black | – | +, 1.1 cm |
| | ethanol 90%, brown-black | – | +, 1.1 cm |
| | ethanol 100%, brown-black | – | +, 1.1 cm |
| Market B2-black henna powder | ethanol 20%, brown + black powder | +, 0.8 cm | +/–, 0.8 cm |

EXAMPLE 4

Operating as in the General Procedures above, methanolic extracts of black henna were tested against *S. epidermidis* and *C. xerosis*. The results are shown in Table V.

TABLE V

| SOURCE & COLOR OF HENNA | EXTRACTION CONDITIONS AND EXTRACT COLOR | INHIBITION OF S.epidermidis | INHIBITION OF C.xerosis |
|---|---|---|---|
| Market B1-black henna powder | methanol 5%, dark brown + black powder | +, 0.5 cm | +/−, 0.3 cm |
| | methanol 10%, dark brown + black powder | +, 0.5 cm | +/−, 0.4 cm |
| | methanol 15%, dark brown + black powder | +, 0.8 cm | +/−, 0.9 cm |
| | methanol 20%, dark brown + black powder | +, 1.3 cm | +/−, 0.9 cm |
| | methanol 25%, dark brown + black powder | +, 1.3 cm | +/−, 0.9 cm |
| | methanol 30%, dark brown + black powder | +, 1.3 cm | +, 1.1 cm |
| | methanol 35%, dark brown + black powder | +, 1.3 cm | +, 1.0 cm |
| | methanol 40%, brown + black powder | +, 1.1 cm | +, 1.1 cm |
| | methanol 45%, brown + black powder | +, 1.1 cm | +, 1.1 cm |
| | methanol 50%, brown + black powder | +, 0.8 cm | +, 0.9 cm |
| | methanol 55%, brown | +, 0.7 cm | +, 0.8 cm |
| | methanol 60%, brown | +, 0.8 cm | +/−, 0.5 cm |
| | methanol 65%, brown | +, 0.8 cm | +/−, 0.5 cm |
| | methanol 70%, brown | +, 0.8 cm | +/−, .5 cm |
| | methanol 75%, dark brown | +, 1.1 cm | +/−, 0.5 cm |
| | methanol 80%, brown-black | +, 0.9 cm | − |
| | methanol 90%, brown-black | +, 0.9 cm | +, 0.8 cm |
| | methanol 100%, brown-black | +, 0.8 cm | +, 0.7 cm |

EXAMPLE 5

Operating as in the General Procedures above, ethanolic extracts of red henna were tested against *S. epidermidis* and *C. xerosis*. The results are shown in Table VI.

TABLE VI

| SOURCE & COLOR OF HENNA | EXTRACTION CONDITIONS AND EXTRACT COLOR | INHIBITION OF S.epidermidis | INHIBITION OF C.xerosis |
|---|---|---|---|
| Market R1-red henna powder | water, orange | +/−, 0.2 cm | +/−, 0.2 cm |
| | ethanol 5%, orange | − | +/−, 0.2 cm |
| | ethanol 10%, orange | − | +/−, 0.5 cm |
| | ethanol 15%, orange | − | +/−, 0.5 cm |
| | ethanol 20%, orange | − | +, 0.8 cm |
| | ethanol 25%, orange | − | +, 0.5 cm |
| | ethanol 30%, orange | − | +, 0.9 cm |
| | ethanol 35%, orange | − | +, 0.9 cm |
| | ethanol 40%, orange-brown | +/−, 0.2 cm | +, 1.0 cm |
| | ethanol 45%, orange-brown | +/−, 0.3 cm | +, 1.0 cm |
| | ethanol 50%, orange-brown | − | +, 1.0 cm |
| | ethanol 55%, orange-brown | +/−, 0.2 cm | +, 0.8 cm |
| | ethanol 60%, orange-brown | +/−, 0.2 cm | +, 1.1 cm |
| | ethanol 70%, brown + black powder | − | +, 1.1 cm |
| | ethanol 75%, dark brown + black powder | − | +, 1.1 cm |
| | ethanol 80%, dark brown + black powder | − | +, 0.5 cm |
| | ethanol 90%, black | − | +, 0.3 cm |
| | ethanol 100%, black | − | +, 0.7 cm |

EXAMPLE 6

Extracts of red and black henna and blue indigo were tested against *C. xerosis, S. epidermidis, Staphylococcus aureus* and *Micrococcus luteus*. The results are shown in Table VII.

TABLE VII

| SOURCE & COLOR OF POWDER | EXTRACTION CONDITIONS | INHIBITION OF C.xerosis | INHIBITION OF S.epidermidis | INHIBITION OF S.aureus | INHIBITION OF Micrococcus luteus |
|---|---|---|---|---|---|
| Market R1-red henna powder | water | +/−, 0.5 cm | +/−, 0.3 cm | +/−, 0.6 cm | − |
| | ethanol 15% | +, 0.6 cm | − | +/−, 0.5 cm | − |
| | ethanol 30% | +, 0.6 cm | − | +/−, 0.5 cm | − |
| | ethanol 50% | +, 0.8 cm | − | − | − |
| | ethanol 70% | +, 1.2 cm | +/−, 0.6 cm | +/−, 0.2 cm | − |
| Market B1-black henna powder | water | +/31 , 0.6 cm | +, 1.7 cm | +, 2.1 cm | − |
| | ethanol 15% | +, 0.8 cm | +, 2.4 cm | +, 2.1 cm | +, 1.3 cm |
| | ethanol 30% | +, 1.1 cm | +, 2.2 cm | +, 2.4 cm | +, 2.0 cm |
| Bengal blue Indigo | ethanol 20% | +, 1.2 cm | +,1.0 cm | +, 0.7 cm | +, 0.8 cm |

EXAMPLE 7

Operating as in the General Procedures above, dipropylene glycol extracts of black henna were tested against *S. epidermidis* and *C. xerosis*. The results are shown in Table VIII.

TABLE VIII

| | CONTROL | | EXPERIMENT | | |
|---|---|---|---|---|---|
| EXTRACTING SOLVENT | INHIBITION OF C. xerosis | INHIBITION OF S.epidermidis | EXTRACTION CONDITIONS OF BLACK HENNA AND EXTRACT COLOR | INHIBITION OF C. xerosis | INHIBITION OF S.epidermidis |
| 10% DPG | − | − | 10% DPG, dark brown + black powder | +, 0.5 cm | +, 0.7 cm |
| 20% DPG | − | − | 20% DPG, dark brown + black powder | +, 0.6 cm | +, 0.8 cm |
| 30% DPG | − | − | 30% DPG, dark brown + black powder | +, 0.6 cm | +, 1.0 cm |
| 40% DPG | +/− | − | 40% DPG, dark brown + black powder | +, 0.7 cm | +, 1.2 cm |
| 50% DPG | +/−, 0.6 cm | − | 50% DPG, dark brown | +, 0.7 cm | +, 0.8 cm |
| 60% DPG | +/−, 0.7 cm | − | 60% DPG, dark brown | +, 0.8 cm | +, 0.9 cm |
| 70% DPG | +/−, 0.7 cm | − | 70% DPG, dark brown | +, 0.7 cm | +, 1.0 cm |
| 80% DPG | +/−, 0.7 cm | − | 80% DPG, dark brown | +/−, 0.7 cm | +/−, 0.6 cm |
| 90% DPG | +, 0.9 cm | − | 90% DPG, brown-green | +/−, 0.9 cm | +/−, 0.6 cm |
| 100% DPG | +, 1.1 cm | − | 100% DPG, green | +/−, 1.1 cm | − |

EXAMPLE 8

Operating as in the General Procedures above, dipropylene glycol extracts of red henna were tested against *S. epidermidis* and *C. xerosis*. The results are shown in Table IX.

TABLE IX

| | CONTROL | | EXPERIMENT | | |
|---|---|---|---|---|---|
| | | | EXTRACTION CONDITIONS OF | | |
| EXTRACTING SOLVENT | INHIBITION OF *C. xerosis* | INHIBITION OF *S.epidermidis* | RED HENNA AND EXTRACT COLOR | INHIBITION OF *C. xerosis* | INHIBITION OF *S.epidermidis* |
| 10% DPG | N.D. | – | 10% DPG, orange | +, 0.4 cm | – |
| 20% DPG | N.D. | – | 20% DPG, orange | +, 0.6 cm | – |
| 50% DPG | +, 0.4 cm | – | 50% DPG, orange | +, 0.6 cm | – |
| 70% DPG | N.D. | – | 70% DPG, brown-orange | +, 0.7 cm | – |
| 100% DPO | +, 0.5cm | – | 100% DPG, green | +, 0.7 cm | – |

EXAMPLE 9

Operating as in the General Procedures above, isopropanol extracts of black henna were tested against *S. epidermidis* and *C. xerosis*. The results are shown in Table X.

TABLE X

| | CONTROL | | EXPERIMENT | | |
|---|---|---|---|---|---|
| | | | EXTRACTION CONDITIONS OF | | |
| EXTRACTING SOLVENT | INHIBITION OF *C. xerosis* | INHIBITION OF *S.epidermidis* | BLACK HENNA AND EXTRACT COLOR | INHIBITION OF *C. xerosis* | INHIBITION OF *S.epidermidis* |
| 10% IP | – | – | 10% IP, dark brown + black powder | +, 0.5 cm | +/–, 0.5 cm |
| 20% IP | +/–, 0.6 cm | – | 20% IP, dark brown + black powder | +, 0.6 cm | +/–, 0.5 cm |
| 30% IP | +/–, 0.9 cm | – | 30% IP, dark brown + black powder | +/–, 0.8 cm | +, 1.2 cm |
| 40% IP | +/–, 1.1 cm | – | 40% IP, dark brown + black powder | +, 1.1 cm | +, 1.6 cm |
| 50% IP | +, 1.3 cm | – | 50% IP, green brown + black powder | +/–, 1.1 cm | +/–, 1.0 cm |
| 60% IP | +, 1.0 cm | – | 60% IP, dark green | +, 1.3 cm | +/–, 0.8 cm |
| 70% IP | +, 1.2 cm | – | 70% IP, dark green | +, 1.4 cm | – |
| 80% IP | +, 1.2 cm | – | 80% IP, dark green | +, 1.4 cm | – |
| 90% IP | +, 1.4 cm | – | 90% IP, dark green | +, 1.5 cm | – |
| 100% IP | +, 1.4 cm | – | 100% IP, green | +, 1.7 cm | – |

EXAMPLE 10

Operating as in the General Procedures above, isopropanol extracts of red henna were tested against *S. epidermidis* and *C. xerosis*. The results are shown in Table XI.

TABLE XI

| | CONTROL | | EXPERIMENT | | |
|---|---|---|---|---|---|
| | | | EXTRACTION CONDITIONS OF RED | | |
| EXTRACTING SOLVENT | INHIBITION OF C. xerosis | INHIBITION OF S. epidermidis | HENNA AND EXTRACT COLOR | INHIBITION OF C. xerosis | INHIBITION OF S. epidermidis |
| 10% IP | N.D. | – | 10% IP, orange | +/–, 1.0 cm | – |
| 20% IP | N.D. | – | 20% IP, orange | +/–, 0.6 cm | – |
| 50% IP | +, 1.0 cm | – | 50% IP, brown + powder | +, 1.2 cm | – |
| 70% IP | N.D. | – | 70% IP, brown-green | +, 0.9 cm | – |
| 100% IP | +, 0.6 cm | – | 100% IP, green | +, 1.0 cm | – |

EXAMPLE 11

A group of ten individuals performed the following experiment. Prior to evening shower, the individuals rubbed their right armpits with a deodorizing composition comprising an oil plus Benzalkonium chloride and red henna and following three minutes showered as usual. Microbial counts were estimated directly before application, and the following morning. Individuals as well as independent judges also scored their own armpit odors and recorded them. The results showed a reduction of 1.5–2 orders of magnitude in bacterial counts in the experimental (right armpit), as compared to no reduction in the control (left armpit).

Similar reductions were observed by the participants in scoring the odor from the armpits, i.e., that the experimental armpit was free or almost free of odor the morning following application, wherease the control armpit had substantial odor.

The results show that this concept is highly effective in long-lasting (ca. 8 hours) reduction of microbial counts and odor levels.

All the above description and examples have been given for the purpose of illustration and are not intended to limit the invention in any way. Many modifications can be made in the compositions of the invention. For instance, different henna powders or purified henna components can be used, many different additives can be incorporated in the compositions of the invention, be they antibacterially active or not, and many different extraction solvents can be used, to provide compositions of different activity, all without exceeding the scope of the invention.

The suitable extraction solvents or solvent combinations are those that when used as described in the extraction process yield an inhibition zone of not less than 3 millimeters when tested on lawns of susceptible bacteria.

What is claimed is:

1. A process for manufacturing a deodorizing and antibacterial composition, comprising extracting a natural material comprising *Indigofera tinctoria* with an extraction solvent to obtain an extract, wherein the extract, optionally admixed with a carrier, is a deodorizing and antibacterial composition.

2. A process according to claim 1, wherein the natural material employed for the extraction process is a red henna.

3. A process according to claim 1, wherein the natural material employed for the extraction process is a black henna.

4. A process according to claim 2 or 3, wherein the natural material employed for the extraction process is a henna powder.

5. A process for manufacturing a deodorizing and antibacterial composition, comprising extracting a natural material comprising a mixture of *Lawsonia inermis* and *Indigofera tinctoria* with an extraction solvent to obtain an extract, wherein the extract, optionally admixed with a carrier, is a deodorizing and antibacterial composition.

6. A process according to claim 1 or 5, wherein the extraction solvent is water, an alcohol, or a mixture of water and an alcohol.

7. A process according to claim 1 or 5, wherein the carrier is water, an alcohol, or an oil-based carrier.

8. A method for deodorizing and preventing the formation of body odors comprising the steps of:

applying a composition comprising an extract of *Indigofera tinctoria* to body parts affected by body odor for a period of time sufficient to inhibit the growth of microorganisms responsible for odor formation; and washing off the composition.

9. The method of claim 8 wherein the composition is applied to the axilla.

10. The method of claim 8 wherein the composition inhibits the growth of microorganisms selected from the group consisting of *Staphylococcus aureus, Staphylococcus epidermidis* and *Corynebacterium xerosis*.

* * * * *